United States Patent

Groves, Jr.

[11] 4,010,185
[45] Mar. 1, 1977

[54] STABLE OIL-SOLUBLE METAL SULFONATE ANALYTICAL STANDARDS

[75] Inventor: William L. Groves, Jr., Ponca City, Okla.

[73] Assignee: Continental Oil Company, Ponca City, Okla.

[22] Filed: May 22, 1975

[21] Appl. No.: 579,761

[52] U.S. Cl. .............................. 260/433; 252/33.4; 252/47.5; 252/408; 260/429 R; 260/429 K; 260/429.5; 260/429.7; 260/435 R; 260/437 R; 260/438.1; 260/439 R; 260/501.21
[51] Int. Cl.² .......................................... C07F 3/12
[58] Field of Search .......... 260/429 R, 429 K, 433, 260/438.1, 435, 439 R, 429.7, 437, 429.5, 501.21; 252/33.4, 47.5, 408

[56] References Cited
UNITED STATES PATENTS

| | | | |
|---|---|---|---|
| 3,005,847 | 10/1961 | Bray | 260/501.21 X |
| 3,351,526 | 11/1967 | Subirana | 260/501.21 X |
| 3,354,201 | 11/1967 | Subirana | 260/501.21 |
| 3,785,976 | 1/1974 | Hunt | 260/429 K X |
| 3,897,470 | 7/1975 | Sias | 260/429 K |

Primary Examiner—Helen M. S. Sneed
Attorney, Agent, or Firm—Cortlan R. Schupbach, Jr.

[57] ABSTRACT

A stable oil-soluble metal sulfonate composition for use as an analytical standard for metal-in-oil analysis is provided. The composition is an equilibrium product represented as follows:

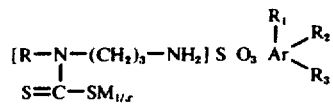

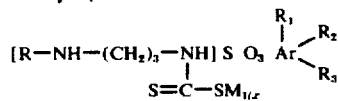

wherein M is a metal selected from the group consisting of mercury, vanadium, iron, lead, barium, berylium, tin, silver, titanium, copper, magnesium and sodium; R, $R_2$ and $R_3$ are alkyl radicals containing from about 10 to 18 carbon each; Ar is an aryl radical; $R_1$ is hydrogen or an alkyl radical containing from 1 to about 4 carbon atoms; x is an integer equal to the chemical valance of M, and the $ArR_1R_2R_3$ constituent is further characterized as being oil-soluble and having an average molecular weight in the range of from about 320 to 720.

4 Claims, No Drawings

STABLE OIL-SOLUBLE METAL SULFONATE ANALYTICAL STANDARDS

BACKGROUND OF THE INVENTION

1. Field of the Invention

This invention relates to improved analytical standard compositions. In one aspect it relates to stable oil-soluble metal sulfonate compositions useful as analytical standards. In yet another aspect the invention relates to stable oil-soluble metal sulfonate analytical standards wherein the metal constituent is mercury, vanadium, iron, lead, barium, berylium, tin, silver, titanium, copper, magnesium, sodium or mixtures thereof.

2. Brief Description of Prior Art

Dispersions containing certain oil-soluble metal sulfonates have acquired considerable importance as additions in fuels and lubricating oil. Such dispersions have been highly useful as additives to other materials for the suspending of insoluble waste materials formed in the utilization of the material and also for corrosion inhibition. When the oil-soluble metal sulfonates are employed as additives for use in internal combustion engine lubricating compositions, such agents function to effectively disperse or peptize the insolubles formed by the fuel combustion, oil oxidation, or similar conditions obtained during the operation of the engine.

In recent years it has been found that superior standards for spectrographic equipment can be prepared from oil-soluble metal sulfonates and metal dispersions in said sulfonates by dissolving such materials in predetermined quantities in a suitable solvent. Such standards have exhibited indefinite shelf life and any combination of metals can be combined without precipitation of the metal constituents.

Thus, while the use of oil-soluble metal sulfonates have been established and recognized, problems have been encountered in the production of stable oil-soluble metal sulfonate compositions for use as an analytical standard for metal-in-oil analysis. Such problems have been even more prevalent in the production and use, as analytical standards, of oil-soluble metal sulfonate compositions of certain metals, such as mercury. For example, a number of oil-soluble mercury compounds have been made or proposed heretofore wherein such compounds are prepared from carboxylates, sulfonates, amines and alkylaryls; but, in all cases, the oil-soluble mercury compound is unstable as indicated by the formation of a grey precipitate.

Further, problems have been encountered in the blend stability of oil-soluble metal sulfonate compositions containing other metals such as molybdenum, vanadium, iron, boron and silver. Such problems have been especially encountered in the blend stability of such metal sulfonates at low metal concentrations, e.i. 100 parts per million or less. Therefore, a need has long been recognized for stable oil-soluble metal sulfonate compositions which can readily be used an analytical standards for metal-in-oil analysis.

OBJECTS OF THE INVENTION

An object of the present invention is to provide oil-soluble metal sulfonate compositions having improved stability.

Another object of the present invention is to provide stable oil-soluble metal sulfonate compositions which can be employed as analytical standards for metal-in-oil analysis.

Another object of the invention is to provide stable analytical standard for metal-in-oil analysis of mercury and other metals.

Yet another object of the invention is to provide an economical, dependable and efficient method for preparing stable oil-soluble metal sulfonate compositions.

These and other objects, advantages and features of the present invention will be apparent to those skilled in the art from a reading of the following detailed description.

DETAILED DESCRIPTION OF THE INVENTION

According to the present invention, I have now discovered a stable oil-soluble metal sulfonate composition which can be used as an analytical standard for metal-in-oil anaylsis. More specifically, the composition is an equilibrium product having the formula

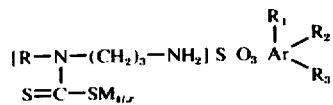

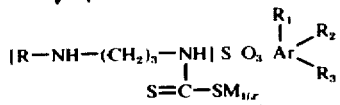

wherein M is a metal selected from the group consisting of mercury, vanadium, iron, lead, barium, berylium, tin, silver, titanium, copper, magnesium and sodium; R, $R_2$ and $R_3$ are alkyl radicals containing from about 10 to 18 carbon each; Ar is an aryl radical; $R_1$ is hydrogen or an alkyl radical containing from 1 to about 4 carbon atoms; x is an integer equal to the chemical valance of M, and the $ArR_1R_2R_3$ constituent is further characterized as being oil-soluble and having an average molecular weight in the range of from about 320 to 720.

The stable oil-soluble metal sulfonate compositions described above can be prepared by adding to a reaction vessel, in the order shown, the following chemical compounds;

a. an alkyl diamine compound represented by the structural formula R-NH-(CH$_2$)$_3$NH$_2$ wherein R is an alkyl radical containing from about 10 to 18 carbon atoms;

b. a diluent;

c. an alkyl substituted aryl sulfonic acid having the structural formula

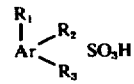

wherein Ar is an aryl radical, $R_1$ is hydrogen or an alkyl radical containing from 1 to 4 carbon atoms and $R_2$ and $R_3$ are alkyl radicals containing from about 10 to 18 carbon atoms each;

d. carbon disulfide; and e. an organic metal salt;

It should be noted that each reaction is allowed to go to substantial completion before the addition of each sequential chemical compound. For example, the reaction between the alkyl diamine compound and the alkyl substituted aryl sulfonic acid is allowed to be substantially complete before the carbon disulfide is added to the reaction mixture. Because of the viscous nature of the sulfonic acid reactant the diluent is employed to facilitate mixing of the reactants. However, it is to be understood that the diluent is inert and does not chemically react with any of the reactants. To better understand the method of producing the stable oil-soluble metal sulfonate compositions of the present invention the following sequence of chemical reactions is set forth. In each reaction the chemical short hand, as to alkyl radicals and the like, is as previously described:

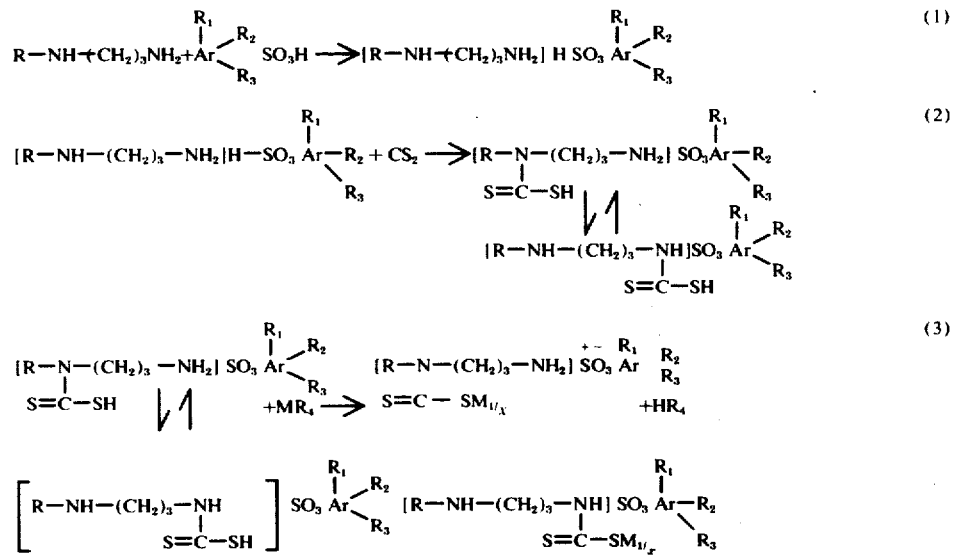

wherein $MR_4$ is an organic salt of the metal desired.

Once the desired product is produced, additional dilutent can be admixed with the product, if desired, so that the product can more readily be filtered to remove insolubles formed during the reaction. The filtrate can then be diluted further to provide a solution containing a desired amount of the metal therein so that same can readily be employed as an analytical standard.

The amount of each constituent employed in the before mentioned chemical reactions can vary widely depending to a large extent on reaction conditions. However, in order to provide a stable product it is desirable that the aklyl substituted diamine and sulfonic acid constituent be employed in stiochemetric amounts. If an excess of the amine constituent is employed the product formed is less stable and on standing, a separation of the metal constituent can be detected by a decrease of the metal constituent in the sample.

As previously stated, the alkyl diamine compound can be any compound having the formula R-NH-$(CH_2)_3$-$NH_2$ wherein R is a alkyl radical containing from about 10 to 18 carbon atoms. However, especially desirable results have been obtained wherein the alkyl moiety is selected from the group consisting of n-coco, n-tallow, n-soya and n-oleyl.

The diluent employed is, as previously stated, an inert liquid which is employed to reduce the viscosity of the reaction mixture. The amount of diluent employed can vary widely and will be dependent on the viscosity of the reactants. Any suitable diluent can be employed, such as pale oil, kerosene, and the like.

The alkyl substituted aryl sulfonic acid constituents employed to produce the oil-soluble sulfonate component are represented by the formula

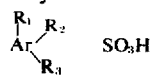

wherein Ar is an aryl radical such as phenyl, and napthyl. $R_1$ is H or an alky radical containing from 1 to about 4 carbon atoms and $R_2$ and $R_3$ are alkyl moieties containing from about 10 to 18 carbon atoms each. In addition, the alkyl substituted aryl radical is characterized as having a molecular weight in the range of from about 320 to 720, preferably in the range of 400 to 480. While any suitable monocyclic or multicyclic aryl radical can be employed, provided the molecular weight of the total radical, which includes the alkyl moieties as previously defined, is within the range set forth above, especially desirable results are obtained when the aryl constituent and $R_1$ cooperate to form an aryl radical selected from the group consisting of benzene, toluene, xylene and napthalene. Further, it is desirable that $R_2$ and $R_3$ contain from about 12 to 14 carbon atoms each.

The reaction between the alkyl diamine compound and the sulfonic acid constituent is carried out at ambient temperature and pressure. However, the reaction mixture is agitated for a period of time sufficient to ensure substantial completion of the reaction between the diamine compound and the sulfonic acid.

Once the desired reaction product has been formed, a stoichiometric amount of carbon disulfide, based on the reaction product of the diamine and sulfonic acid constituents, is added to the reaction product. The resulting mixture is thoroughly agitated until the desired reaction, set forth in Equation 2, has occurred. Thereafter, an organic salt of a metal is admixed with the sulfur containing reaction product and the reaction allowed to proceed, under agitation, until the desired oil-soluble metal sulfonate has been formed. The reaction between the sulfur containing reaction product and the organic salt compound is an ion interchange reaction which is most effectively carried out under the influence of temperature. Thus, it is desirable that the ion interchange reaction be carried out at a temperature in the range of from about 20° to 90° C. However, I have found that in the case of mercury insurance against the conversion of the organic mercury compound to an inorganic form is maintained when the ion interchange reaction is carried out at a temperature from about 25° to 50° C.

As previously stated, the metal ion to be transferred can be mercury, vanadium, iron, lead, barium, beryllium, tin, silver, titanium, copper, magnesium, and sodium. However, the method for producing the desired oil-soluble metal sulfonate compositions of the invention is particularly effective when the metal ion to be transferred is mercury or copper. Examples of suitable organic salts containing the desired metal ions, which can be employed to produce the compositions of the present invention are metal acetate materials such as mercuric acetate, cupric acetate, tributyltin acetate, silver acetate, lead acetate, tributyllead acetate and the like.

In the formation of the oil-soluble metal sulfonate compositions of the present invention one may experience difficulties due to the low solubility of organic salts of certain metals. For example, when cupric acetate is employed as the salt constituent a solubilizer, such as methyl cellosolve, must be incorporated into the reaction mixture so that the before mentioned ion exchange reaction (Equation No. 3) can efficiently proceed. While the amount of the solubilizer employed can vary widely, it is generally desirable that only sufficient solubilizer be incorporated to obtain miscibility of the organic salt with the reaction mixture. Solubilizer, which can be employed are well known in the art and include low molecular weight alcohols such as methanol, ethanol, isopropanol and the like; low molecular weight esters such as ethyl acetate; and low molecular weight ketones such as acetone, methylethyl ketone and the like.

The reaction product so formed is then diluted with from about 20 to 50 weight percent of the inert hydrocarbon diluent in which the oil-soluble metal sulfonate composition is soluble. The diluent, as previously described, is a petroleum derived diluent. Especially desirable results are obtained when the diluent is selected from the group consisting of pale oil and kerosene. The resulting solution is then purified to remove acid constituents formed during the ion interchange reaction. The purified product can then be further diluted with the diluent to produce a solution having a predetermined amount of the stable oil-soluble metal sulfonate compositions of the present invention. Preferably, the metal sulfonate constituent in the diluent will be present in an amount to provide less than 100 parts per million metal in the solution.

In order to more fully illustrate the nature of the present invention, the following experimental data is given. However, it is to be understood that the experimental data is for illustrative purposes only and are not intended to unduly limit or restrict the present invention.

EXAMPLE

One mole of an alkyl substituted diamine having the formula $R\text{-HN-}(CH_2)_3\text{-}NH_2$ wherein R is a linear alkyl radical containing 12 carbon atoms is admixed, under mechanical agitation, with an equal weight of 80 Pale oil diluent. The diamine is a commercially available compound known as Duomeen C.D. One mole of an oil-soluble alkylbenzene sulfonic acid having an average molecular weight of about 500 was then added to the diluted diamine compound. The reaction between the diamine and sulfonic acid constituent was carried out at ambient temperature for a sufficient period of time to allow the formation of one mole of a diamine monosulfonate. (See Equation 1).

One mole of carbon disulfide was then added to the reaction mixture of the diamine monosulfonate. The reaction, which is again carried out at ambient temperature, allows the carbon disulfide to react with the unreacted amine group thus producing one mole of a diamine sulfonate dithiocarbamic acid. (See Equation 2.)

To the diamine sulfonate, dithiocarbamic acid reaction product was added one equivalent weight of mercuric acetate. This reaction proceeded at a moderate rate and the temperature of the reaction was controlled externally at about 50° C. The reaction product, the mercuric salt of the dithiocarbamic acid, became black as the mercuric acetate was spent. (See Equation 3). Once the reaction had gone to completion, low molecular weight side reaction products were removed by employing a vacuum on the reaction system while same is maintained at the reaction temperature and under vigorous agitation.

This recovered product, which had a high viscosity, was diluted with additional pale oil to form a solution containing from 1 to 3 weight percent mercury so that the solution could be readily filtered to remove insoluble equilibrim products. The filtrate was allowed to stand for several days and then refiltered to remove any additional insoluble materials formed. Analytical dilutions were then made, using kerosene as the diluent, and the samples were analyzed for mercury content. The results of such data are as follows:

First analysis — 0.45 weight percent Hg

Analysis after 6 weeks — 0.44 weight percent Hg.

A similar experiment was conducted using cupric acetate rather than the mercuric acetate. In this experiment Blandol N.F., a commercially available white oil, was employed as the initial diluent. In addition, an effective amount (13.7 grams) of a solubilizer was added to the reaction mixture prior to the addition of the cupric acetate (10.0 grams) to insure its solubility in said mixture. The solubilizer employed was methyl cellosolve. The resulting product, which, after filtration, contained 1.41 weight percent copper. Analytical dilutions were made employing 80 pale oil as the diluent. The dilutions were then analyzed and revealed that such dilutions contained 0.5 weight percent copper. Thereafter additional dilutions were made which contained 100 ppm copper. The stability of the analytical standard was then observed over a period of months and found to be excellent.

Throughout the specifications and claims the chemical shorthand usually expressed as $(A)_xM$ is for convenience and brevity expressed as $AM_{1/x}$. Both notations are to be considered as the same for the purpose of the present invention.

Having thus described the invention, I claim:
1. A stable oil soluble metal sulfonate analytical standard prepared by sequentially reacting
   a. an alkyl diamine compound represented by the structural formula $R\text{-NH-}(CH_2)_3\text{-}NH_2$ wherein R is an alkyl group containing from about 10 to 18 carbon atoms;
   b. an inert diluent;
   c. an alkyl substituted aryl sulfonic acid having the structural formula

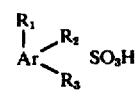

wherein Ar is an aryl group, $R_1$ is hydrogen or an alkyl group containing from about 1 to 4 carbon atoms and $R_2$ and $R_3$ are alkyl groups containing from about 10 to 18 carbon atoms each;

d. carbon disulfide; and e. an organic metal acetate wherein the metal is selected from the group consisting of mercury, vanadium, iron, lead, barium, beryllium, tin, silver, titanium, copper, magnesium, and sodium.

2. The composition of claim 1 wherein R is a mixture of linear alkyl groups selected from the group consisting of saturated alkyl moieties and unsaturated alkyl moieties; $R_2$ and $R_3$ are linear alkyl groups containing from about 12 to 14 carbon atoms; Ar is a aryl group selected from the group consisting of phenyl and napthyl; and the average molecular weight of said Ar, $R_1$, $R_2$, $R_3$ constituent is from about 400 to 480.

3. The composition of claim 2 wherein M is selected from the group consisting of mercury and copper.

4. The composition of claim 3 wherein $R_1$ is hydrogen.

* * * * *